(12) United States Patent
Grabowy et al.

(10) Patent No.: US 7,063,658 B2
(45) Date of Patent: Jun. 20, 2006

(54) SYSTEM HAVING A CARRIER SUBSTRATE AND A TI/P OR A1/P COATING

(76) Inventors: Udo Grabowy, Rauchschwelbenweg 8, Emskirchen-Flamersheim 53881 (DE); Heinz Werner Busch, Auelweg 2, 53639, Königswinter-Thomasberg (DE)

(*) Notice: Subject to any disclaimer, the term of this patent is extended or adjusted under 35 U.S.C. 154(b) by 16 days.

(21) Appl. No.: 10/296,599

(22) PCT Filed: May 5, 2001

(86) PCT No.: PCT/EP01/05610

§ 371 (c)(1),
(2), (4) Date: Jun. 5, 2003

(87) PCT Pub. No.: WO01/91823

PCT Pub. Date: Dec. 6, 2001

(65) Prior Publication Data

US 2003/0191354 A1     Oct. 9, 2003

(30) Foreign Application Priority Data

May 29, 2000  (DE) ................................ 100 26 485

(51) Int. Cl.
*A61N 5/00*     (2006.01)
(52) U.S. Cl. ........................................................ 600/1
(58) Field of Classification Search ................ 600/1–8; 29/527.1, 401.1; 606/108, 139, 191, 198, 606/194, 130; 623/1, 12; 424/1.29, 422; 427/527, 38; 356/312, 85; 376/158, 169, 376/184, 186, 202; 429/38, 527
See application file for complete search history.

(56) References Cited

U.S. PATENT DOCUMENTS

| | | | | |
|---|---|---|---|---|
| 5,342,283 A | * | 8/1994 | Good | 600/8 |
| 5,871,437 A | | 2/1999 | Alt | 600/3 |
| 5,919,126 A | | 7/1999 | Armini | 600/3 |
| 6,010,445 A | | 1/2000 | Armini et al. | 600/3 |
| 6,059,714 A | * | 5/2000 | Armini et al. | 600/3 |
| 6,060,036 A | * | 5/2000 | Armini | 424/1.29 |
| 6,099,457 A | * | 8/2000 | Good | 600/8 |
| 6,183,409 B1 | * | 2/2001 | Armini | 600/3 |
| 6,347,443 B1 | * | 2/2002 | Coniglione | 29/401.1 |

FOREIGN PATENT DOCUMENTS

| | | |
|---|---|---|
| DE | 43 15 002 | 8/1994 |
| EP | 0 433 011 | 6/1991 |
| EP | 0 539 165 | 4/1993 |

OTHER PUBLICATIONS

"Vakuumbeschichtung1, Plasmaphysik-Plasmadiagnostik-Analytik", (Vacuum coating 1, Plasma Physics-Plasma Diagnostics-Analytics), Dr. Ing. Hartmut Frey, VDI Verlag, Dusseldort 1995, ISBN No. 3-540-62265-9, p. 1-170 and 233-285.

"Elektronik und Mikroelektronik" (Electronics and Microelectronics), Dieter Sautter and Hans Weinerth, VDI-Verlag 1990, p. 804-807.

* cited by examiner

*Primary Examiner*—Samuel G. Gilbert
(74) *Attorney, Agent, or Firm*—Taylor & Aust, P.C.

(57) ABSTRACT

The invention refers to a system having a substrate as carrier and a coating deposited on the substrate.

Figure 1:
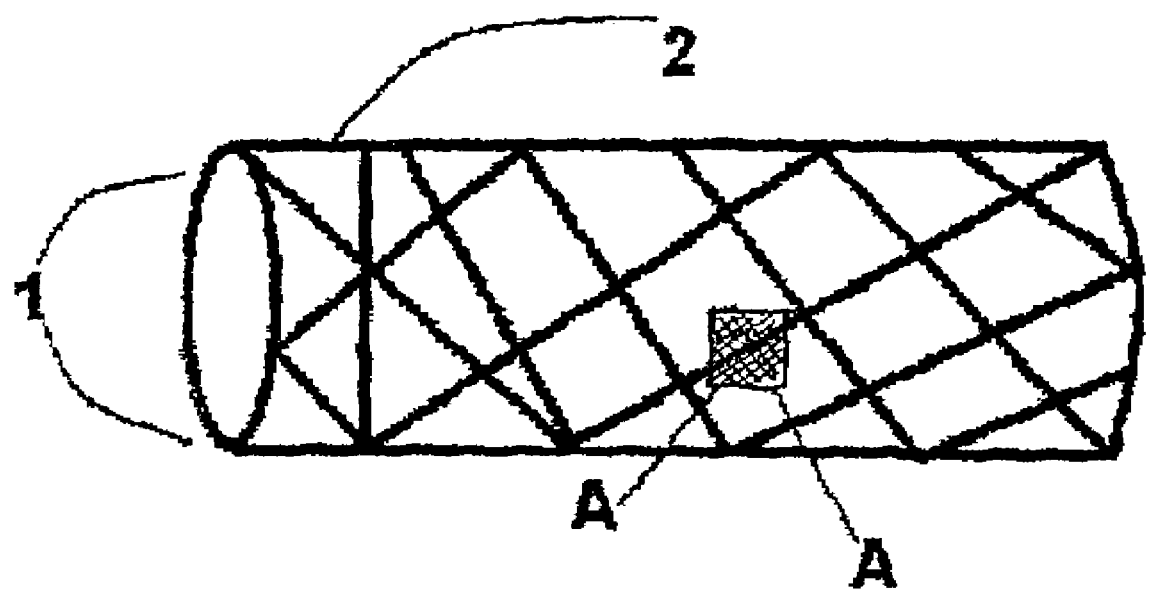

The invention is characterized in that the coating comprises at least the elements titanium (Ti) or aluminum (Al), respectively, and phosphorus (P).

18 Claims, 3 Drawing Sheets

SYSTEM HAVING A CARRIER SUBSTRATE AND A TI/P OR A1/P COATING

The invention refers to a system having a substrate as carrier and a coating deposited on the substrate as well as a process for depositing such a coating in a sputter plant, in particular in a PVD or PECVD sputter plant, respectively, and an implant, in particular a vascular implant, comprising such a system or coating, respectively, produced by sputter deposition in such a sputter plant.

Systems having a substrate as carrier and coatings deposited on the substrate are known in many fields of technology, for example in telecommunications technology.

In this respect, reference is for example made to the following publication "Vakuumbeschichtung 1, Plasmaphysik-Plasmadiagnostik-Analytik", (Vacuum coating 1, plasma physics-plasma diagnostics-analytics), published by Dr.Ing. Hartmut Frey, VDI Verlag, Düsseldorf 1995. A large number of processes have become known for depositing the coating on a substrate carrier. One process for depositing coatings is sputter deposition. According to the encyclopedia "Elektronik und Mikroelektronik" (electronics and microelectronics) published by Dieter Sautter and Hans Weinerth, VDI-Verlag 1990, p. 804–807, sputtering or cathode evaporation is understood to be a physical process with which any material in solid form can be deposited on any substrate as a coating having good adhesive properties. In silicon-semiconductor technology, above all metallizing coatings for contacts and conducting paths as well as passivating coatings for the protection of finished integrated circuits are produced using sputter processes.

By the sputter process itself, the carriers to be coated are only heated to relatively low temperatures.

The principle of sputter deposition works such that an inert gas plasma, preferably argon plasma, is produced in a vacuum chamber at low pressure, the positively charged inert gas ions from the plasma are accelerated towards the negatively biased target, consisting of the material to be deposited, as a result of an electric field and the material is ejected from the target by the impact of the inert gas ions, which is deposited on the opposing surface of the substrate to be coated.

There is a large number of different sputter plants e.g. DC-voltage planar diode sputter plants, high frequency sputter plants as well as BIAS sputter plants. As regards the design of different sputter plants, reference is again made to the "Lexikon Elektronik und Mikroelektronik" cited above. In order to obtain a high plasma density directly at the surface of the target, so-called magnetron targets can be used which are characterized in that, by suitably arranging a magnetic field close to the surface of the target, a high plasma density directly at the surface of the target is reached within the area in which the magnetic field is strong enough. By using a magnetron target, the sputter rate can be decisively increased as compared to the use of a normal target. By varying the gas pressure the properties of the coating can be varied at a constant sputter rate.

As regards the different sputter techniques, reference is made to the "Lexikon Elektronik und Mikroelektronik, cited above", the contents of disclosure of which is included in the present application to its full extent.

Vascular implants for reducing and/or removing vascular contractions and containing at least one radionuclide species are known from the following publications:

DE-C-4315002
EP-A-0433011
EP-A-0539165

For activating the vascular implants according to DE 4315002, an external beam of a cyclotron with 9.2 MeV deuterons is used. As a result of the bombardment with a directed deuteron beam, a high proportion of radionuclides with electron capture transitions and soft X-radiation resulting therefrom as well as $\beta_+$-transitions are induced in the CrNi steel of the stent according to DE 4315002.

In this process it is in particular disadvantageous, in addition to the high expenditure, that activation is created to a volume of up to some micrometers depth by the bombardment with radioactive radiation particles. Thus radioactive nuclei are also located directly at the surface. These can emerge when contacted for example with blood and result in a radioactive danger to the patient.

A further disadvantage is the low yield during irradiation.

Thus, the production of a vascular implant according to the prior art of DE 4315002 requires a careful and intensive subsequent treatment of the surfaces in order to prevent uncontrolled escaping of radioactivity into the body.

It is thus the object of the invention to provide a coating system which is improved in comparison with the prior art and which is characterized by a high biocompatibility and avoids the disadvantages of the prior art during irradiation with for example neutrons for producing a radioactive vascular implant.

According to the invention, this object is achieved in that, in a system with a substrate as carrier and a coating deposited on the substrate, the coating comprises at least the elements titanium (Ti) or aluminum (Al) and phosphorus (P).

As substrate materials in particular all materials are conceivable which can be used in medicine and which can be provided with a coating. The following shall be mentioned only as examples: metals, metal alloys, glass and plastics.

The coating preferably further comprises nitrogen (N) as well as a metal preferably selected from one of the following elements:

Si, GE, W, Pt, Pb, Co, Sm, Ir, Re.

The proportion of phosphorus of the coating is preferably 35 atomic % at the most, with a composition of less than 5 atomic % phosphorus already resulting in a good adhesion on the substrate and a lowering of stress of the coating. In case of a content of phosphorus of between 5 and 10 atomic %, abrasion properties similar to the TiN are achieved in the coating in addition to the lowering of stress.

If the coating is to exhibit a high mechanical load capacity, a proportion of weight of 10 atomic % phosphorus (P) is preferably adjusted. Coatings with a proportion of from 20 atomic % to 35 atomic % phosphorus exhibit a lower mechanical load capacity. The high contents of phosphorus, as described in the following, can be activated with the aid of a suitable neutron flux.

The coating thickness of the coating according to the invention lies between 10 nanometers (nm) and 20 micrometers (μm), with the coating thickness of up to 0.5 micrometer serving for creating biocompatibility and coating thickness of between 0.5 micrometer and 20 micrometers being suitable for use in neutron activation in the production of a radioactive stent.

In order to employ the coatings as carriers of medical drugs, it is advantageous if the coatings exhibit a high porosity, preferably between 1 to 4 micrometers.

The porosity of the coating can be adjusted by selecting the coating parameters substrate angle, substrate temperature, acceleration voltage and plasma power.

A coating process is preferably produced using a magnetron-sputter-plant with a process gas from Ar—N.

As carriers for the coating, materials for vascular implants made of pure titanium or memory alloys, for example nitinol, or a Ni—Ti—alloy, are used. In principle, all such elements which do not or only to a very small extent form active isotopes when bombarded with thermal neutrons and the activity products of which decay already after a short decay time, which lies preferably within few hours, to an extent which can be neglected, can be employed as carrier materials when using such systems for producing radioactive implants.

In a particularly advantageous embodiment of the invention, a coating of Ti—Al—N—P, Ti—N—P or Al—N—P, respectively, is uniformly first deposited on the carrier at a coating thickness in the range of between 1 and 3 micrometers.

On this coating, a thin overcoat of TiN or amorphous carbon is deposited in order to seal off the subjacent functional coating of Ti—Al—N—P, Ti—N—P or Al—N—P, respectively. The coating thickness of the second coating is only few nanometers and is characterized by a particularly good biocompatibility. The second coating forms a diffusion barrier for the subjacent activated functional coating.

In addition to the coating system, the invention also refers to a process for coating a substrate with a coating comprising titanium and phosphorus by sputter deposition in a sputter plant comprising a vacuum chamber.

A generic process for sputter deposition in a sputter plant is sufficiently known from the prior art, for example in the form of Dieter Sautter, Hans Welmerth, "Lexikon Elektronik und Mikroelektronik", p. 804–806, cited above, with the contents of disclosure of this citation being included in the present application to its full extent.

The process according to the invention is characterized in that a Ti—Ti$_2$—P—M$_x$ or a Ti—Ti$_2$—P mixed target is used as sputter target, with M$_x$ being a metal, preferably Si, Ge, W, Pt, Pb, Co, Sm, Ir, Re, or an Al—Ax—P mixed target, respectively with Ax signifying one or several random elements.

In a preferred embodiment of the invention, the sputter target according to the invention is a target with a titanium base in which bore holes are embedded. In these bore holes pellets are in turn placed, which are for example pressed from a Ti—P—Al powder mixture at a high pressure. The stoichiometry of the target, for example the number of pellets, is now adjusted such that, at a low process temperature of for example 200° C., a very hard coating is created of for example 1800 Vickers hardness with a little stress behavior—compressive stress—of for example 1.5 GPa during sputter deposition. The contents of P in the coating is preferably between 4 to 12 atomic %.

Argon is preferably used as process gas at a pressure of $1-5\times10^{-3}$ mbar. The process is preferably conducted such that nitrogen is introduced into the vacuum chamber with a pressure of $1-5\times10^{-3}$ mbar as a further process gas.

During the coating, the substrate is preferably held at a voltage of from 15 to 25 Volt.

The coating system according to the invention is preferably used as implant, in particular as vascular implant, for example as stent, with the process according to the invention being preferably used as coating process.

The activation of the implant coated according to the invention is achieved by irradiation with neutrons. For this, a vascular implant, for example a stent consisting of nitinol, titanium or platinum and being provided with a coating according to the invention having a thickness of from 0.5 micrometer to 5 micrometers, is exposed to a thermal neutron flux of from $10\times10^{13}$ to $5\times10^{15}$ neutrons*sec$^{-1}$*cm$^{-2}$ for one hour up to 72 hours. The phosphorus $^{31}$P contained in the coating is converted into the β-active isotope $^{32}$P by the neutron bombardment. This corresponds to a β-activity of approximately 50 to 350 kBq per implant, with the γ-activity lying below 10 kBq.

Figure 2:
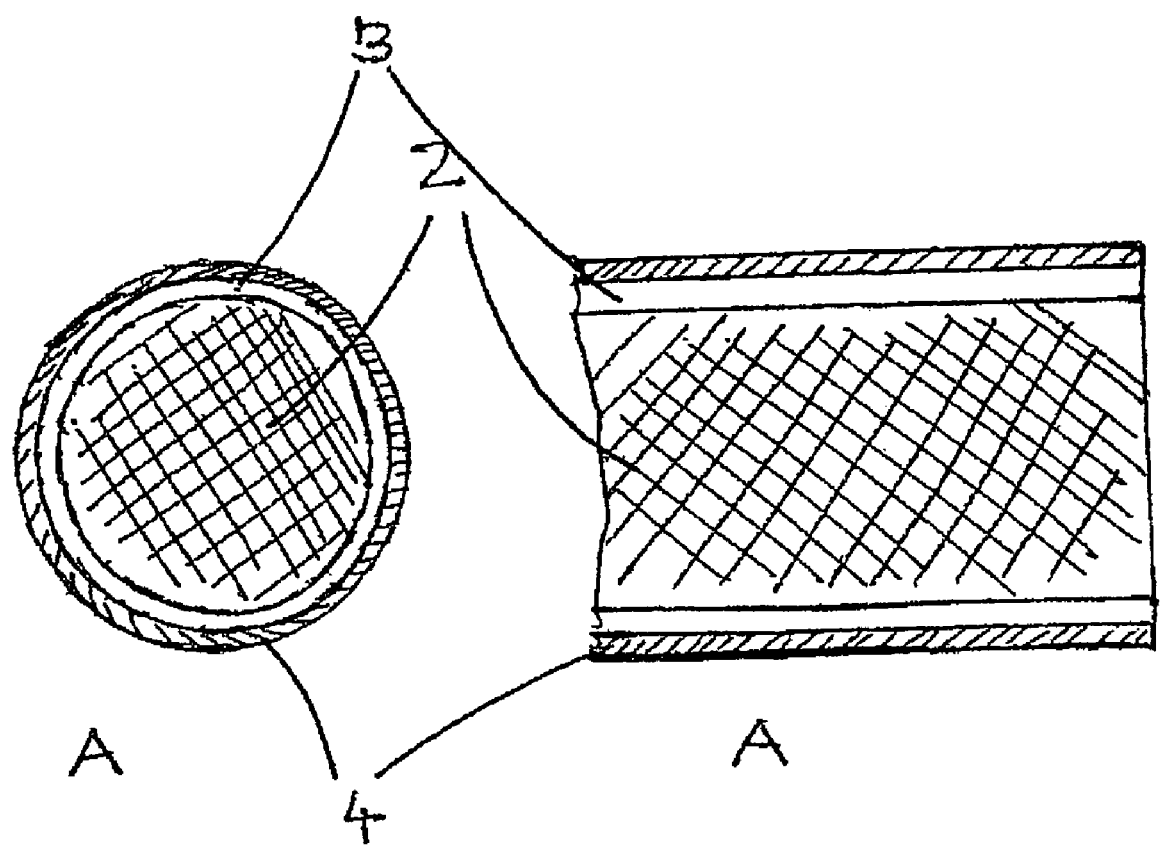
Figure 3:
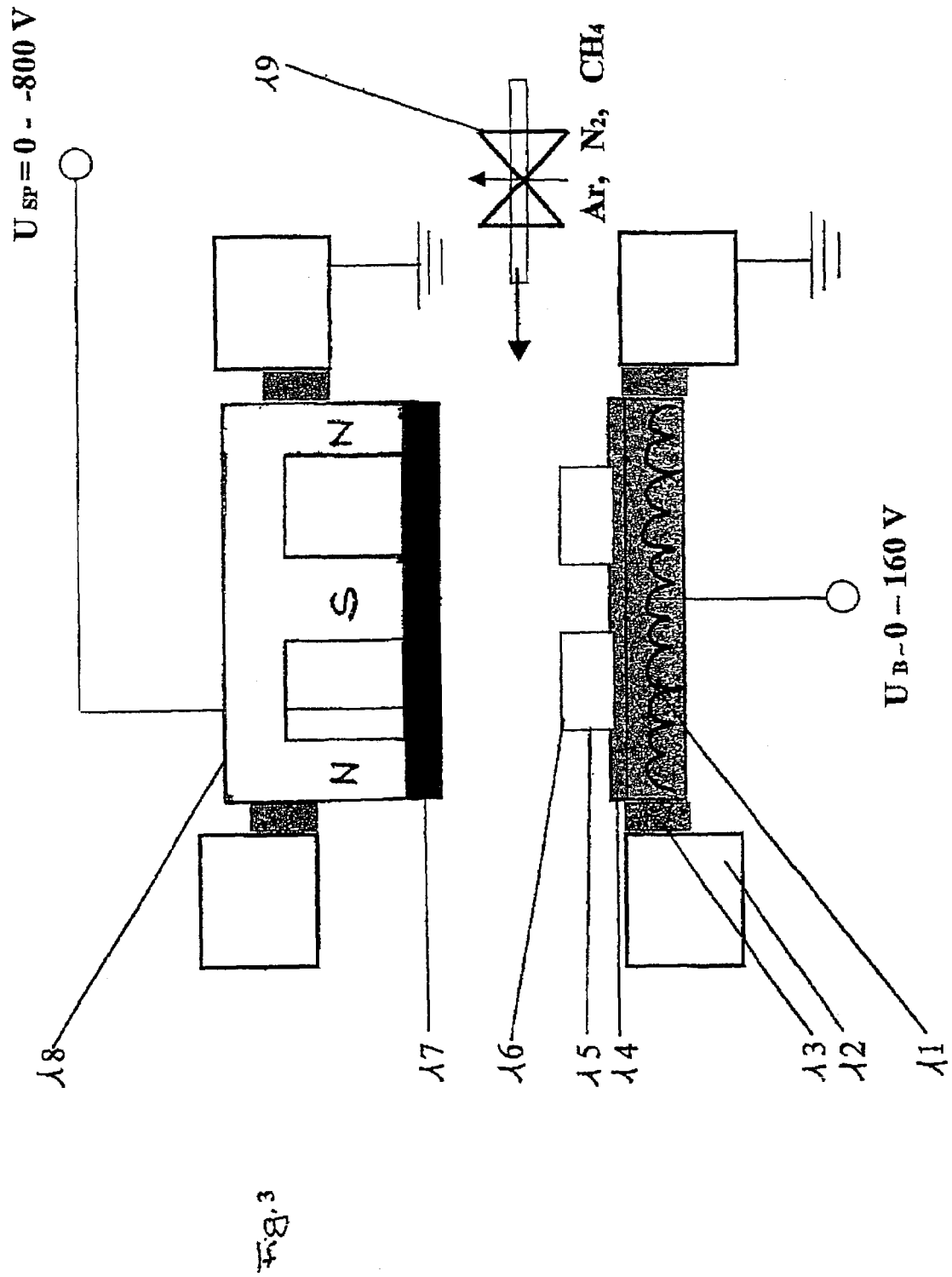

The invention shall be described in the following by way of example using the drawings and embodiments. It is shown in FIG. 1 a nitinol stent;

FIG. 2 a cross section and a longitudinal section of a stent ridge from FIG. 1;

FIG. 3 a magnetron sputter plant for coating a substrate with the process according to the invention.

In FIG. 1 a nitinol stent is depicted. The stent comprises a number of ridges 2 connected with each other in a web-like manner. In this, the base 1 formed by the web represents a cylinder having a circular cross-section. On the ridges 2 as substrate, a coating with the elements titanium and phosphorus is deposited according to the invention. The width of the ridge is 200 micrometers.

A particularly preferred coating, comprising a functional coating and a final coating, with the final coating acting as diffusion barrier, is represented in the longitudinal or axial section, respectively, by a ridge 2 in FIG. 2. The nitinol ridge base 2 having a diameter of 200 micrometers can be seen. The phosphorus—containing titanium-aluminum-nitride— or titanium-nitride coating 3, respectively, is directly deposited on the ridge base 2. The coating thickness preferably amounts to 3 micrometers during deposition and the proportion of phosphorus activated during irradiation with neutrons amounts to 7 to 9 atomic %. Radially around this coating 3, the titanium-nitride-coating 4 can be seen which is free of activity after a neutron activation and which has a thickness of from 20 to 40 nanometers during deposition and acts as diffusion barrier.

By this representation is shown that the β-radiation is emitted radially and uniformly into the material surrounding the stent.

FIG. 3 shows a magnetron-sputter plant for coating a substrate using the process according to the invention. A recipient can be seen with a recipient wall 12, an isolator 13, a substrate carrier 14 and a target 17. The recipient can be evacuated to $1\times10^{-6}$ mbar. Via a valve 19, process gas can be introduced into the recipient. In the recipient a plasma burns wherein positively charged ions are accelerated towards the target 17—the cathode—, with the target being negatively biased.

Atoms are detached from target 17 as a result of the ion bombardment, which are then deposited on a substrate 15—e.g. a stent. The layered structure is thereby obtained.

Behind the target 17, a magnet 18 is arranged which concentrates the plasma in front of the cathode. A higher detachment rate can be reached by the higher ion density obtained thereby, which again results in a faster growth of the coating.

A heating 11 can be advantageously arranged at the substrate which can influence the growth of the coating.

In the following, the embodiment of a stent coated according to the invention is described for a further explanation of the invention:

Embodiment 1

Commercially available stents from the firm MeKo consisting of a nickel-titanium-alloy-nitinol—were coated. The stents had a length of 25 mm, a diameter of 5 mm in the expanded state, the stents being self-expanding. The thickness of the material of the ridges amounted to 200 micrometers.

The coating consisted of titanium-aluminum-phosphorus-nitride or of titanium-phosphorus-nitride, respectively, with the coating being carried out as follows:

First, the recipient was evacuated to a residual pressure of $1 \times 10^{-5}$ millibar. Subsequently, argon was introduced with a pressure of $p(Ar)=1 \times 10^{-2}$ millibar in order to purify the substrate—sputter purification.

In the actual coating step, argon was reduced to $p(Ar)=1, 8 \times 10^{-3}$ millibar and at the same time, nitrogen was introduced with a pressure of $p(N)=8 \times 10^{-4}$ millibar.

The target was a TiP mixed target with the contents of phosphorus amounting to 15%, the sputter voltage being at plus 400 Volt and the substrate being connected to a bias voltage of −15 Volt.

Under these conditions, an evaporation rate of 1 micrometer/hour resulted. The substrate temperature was at 240° C. The proportion of the phosphorus, which was the isotope with the mass-number M=31, in the coating was from 7 to 9 atomic %. As an outer coating a pure titanium-nitride-coating having a thickness of approximately 20 to 40 nanometers was deposited.

The coated stents were exposed to a thermal neutron flux of $3 \times 10^{13}$/second for 24 hours. The flux of fast neutrons was lower by a factor of 500.

By capturing neutrons, the phosphorus isotope $^{31}P$ having a neutron absorption cross-section of 0.16 barn is converted into the β-active isotope $^{32}P$ having a half-life of 14.26 days.

By the direct n,p-nuclear reaction with faster neutrons, further short-lived γ-active radioisotopes are created essentially by the impurities in the titanium and by the nickel isotopes. The main activity lies in the X-ray range and decreases to an extent comparable to a natural activity after a decay time of 3 days. In this, the activity was measured as follows:

The activated samples were measured with a high-resolution X-ray- and a gamma-detector (germanium) after one, seven and thirty days after the activation at the reactor had been carried out. The distance between the sample and the detector was 5 cm. The measured values were corrected taking the detector efficiency and the solid angle into consideration so that the stated values are to be understood as total activities.

The β-starting activity amounted to 50 kBq. The residual activity of all other radioactive isotopes amounts to less than 1 kBq.

Due to the neutron activation of the coating adjacent the substrate it is achieved that the stent is activated in an absolutely uniform manner. The Ti—Ni-coating or DLC (aC:H), respectively, lying outside, acts as diffusion barrier and prevents radioactive isotopes from escaping into the organism.

With the invention, a coating system is provided for the first time which can be radioactively activated in a simple manner, which is characterized by a high biocompatibility, little bacterial adhesion, excellent mechanical properties as well as little abrasion. Furthermore, the vascular implant can again be irradiated in a reactor when the radioactivity decreases and can thus be reused.

The invention claimed is:

1. A medical device comprising:
    a substrate;
    a functional coating deposited on said substrate, said functional coating comprising:
        at least one of titanium and aluminum; and
        neutron activateable phosphorus; and
    an overcoat applied over said functional coating, said overcoat being substantially free of activity after neutron activation;
    wherein said functional coating is one of a titanium-aluminum-nitrogen-phosphorus, a titanium-nitrogen-phosphorus and an aluminum-nitrogen-phosphorus coating.

2. The medical device of claim 1, wherein said functional coating is a sputter coating deposited on said substrate.

3. A medical device comprising:
    a substrate;
    a functional coating deposited on said substrate, said functional coating comprising:
        at least one of titanium and aluminum; and
        neutron activateable phosphorus; and
    an overcoat applied over said functional coating, said overcoat being substantially free of activity after neutron activation;
    wherein said overcoat is one of titanium-nitrogen and an amorphous carbon coating.

4. The medical device of claim 3, wherein said substrate is in the form of a vascular implant made of at least one of substantially pure titanium, a memory alloy and a nickel-titanium alloy.

5. The medical device of claim 4, wherein said memory alloy is nitinol.

6. The medical device of claim 3, wherein said functional coating includes at least one of the elements Si, Ge, W, Pt, Pb, Co, Sm, Ir and Re.

7. A medical device comprising:
    a substrate;
    a functional coating deposited on said substrate, said functional coating comprising:
        at least one of titanium and aluminum; and
        neutron activateable phosphorus; and
    an overcoat applied over said functional coating, said overcoat being substantially free of activity after neutron activation;
    wherein a proportion of said neutron activateable phosphorus amounts to no more than 35% by atomic weight of said functional coating.

8. The medical device of claim 7, wherein said proportion of said neutron activateable phosphorus amounts to no more than 20% by atomic weight of said functional coating.

9. The medical device of claim 8, wherein said proportion of said neutron activateable phosphorus amounts to no more than 10% by atomic weight of said functional coating.

10. The medical device of claim 9, wherein said proportion of said neutron activateable phosphorus amounts to no more than 5% by atomic weight of said functional coating.

11. The medical device of claim 7, wherein said functional coating has a thickness of between approximately 10 nanometers and approximately 20 micrometers.

12. The medical device of claim 7, wherein the medical device is a vascular implant.

13. A medical device comprising:
    a substrate;
    a functional coating deposited on said substrate, said functional coating comprising:
        at least one of titanium and aluminum; and
        neutron activateable phosphorus; and
    an overcoat applied over said functional coating, said overcoat being substantially free of activity after neutron activation;

wherein said functional coating has a porosity of between approximately 1 to approximately 4 micrometers.

14. A radioactive implant, comprising:
a substrate;
a functional coating deposited on said substrate, said functional coating comprising:
  at least one of titanium and aluminum; and
  neutron activateable phosphorus;
an overcoat applied over said functional coating, said overcoat being substantially free of activity after neutron activation;
wherein the radioactive implant is irradiated with a thermal neutron flux of from approximately $1 \times 10^{13}$ neutrons to approximately $5 \times 10^{15}$ neutrons.

15. The process of claim 14 wherein said thermal neutrons flux has a ratio of thermal neutrons to fast neutrons of greater than 100:1.

16. The radioactive implant of claims 15, wherein the duration of irradiation lies between approximately one hour and approximately 72 hours.

17. The radioactive implant of claim 14, wherein the irradiation occurs in such a manner that the dose rate lies between 0 Gy and 250 Gy/cm$^2$ implant surface.

18. The radioactive implant claim 14, wherein the radioactive implant is a β-active implant.

* * * * *

UNITED STATES PATENT AND TRADEMARK OFFICE
CERTIFICATE OF CORRECTION

| | | |
|---|---|---|
| PATENT NO. | : 7,063,658 B2 | |
| APPLICATION NO. | : 10/296599 | |
| DATED | : June 20, 2006 | |
| INVENTOR(S) | : Grabowy et al. | |

It is certified that error appears in the above-identified patent and that said Letters Patent is hereby corrected as shown below:

Title Page
    In the Title, please delete "TI/P or A1/P", and substitute therefore --Ti/P or AI/P--; and In the Abstract, please delete the entire Abstract and substitute therefore the Abstract attached hereto.

ABSTRACT OF THE DISCLOSURE

The invention refers to a system having a substrate as a carrier and a coating deposited on the substrate. The invention is characterized in that the coating includes at least the elements titanium (Ti) or aluminum (Al) and phosphorus (P).

Signed and Sealed this

Eighteenth Day of September, 2007

JON W. DUDAS
*Director of the United States Patent and Trademark Office*